United States Patent [19]

Hester, Jr.

[11] B 3,993,660
[45] Nov. 23, 1976

[54] 2-[3-(PHTHALIMIDOMETHYL)-5-METHYL-4H-1,2,4-TRIAZOL-4-yl]BENZOPHENONES

[75] Inventor: Jackson B. Hester, Jr., Galesburg, Mich.

[73] Assignee: The Upjohn Company, Kalamazoo, Mich.

[22] Filed: May 20, 1974

[21] Appl. No.: 471,494

[44] Published under the second Trial Voluntary Protest Program on March 16, 1976 as document No. B 471,494.

Related U.S. Application Data

[62] Division of Ser. No. 332,377, Feb. 14, 1973, abandoned.

[52] U.S. Cl. ............................................. 260/308 R
[51] Int. Cl.$^2$ ...................................... C07D 403/06
[58] Field of Search ............................... 260/308 R

[56] References Cited

UNITED STATES PATENTS

| | | | |
|---|---|---|---|
| 3,842,089 | 10/1974 | Hester et al. | 260/308 R |
| 3,856,792 | 12/1974 | Hester | 260/308 R |

*Primary Examiner*—Alton D. Rollins
*Attorney, Agent, or Firm*—Hans L. Berneis

[57] ABSTRACT

A process to make 6-phenyl-4H-s-triazolo[4,3-a][1,4]-benzodiazepines by converting 2-[3-(hydroxymethyl)-4H-1,2,4-triazol-4-yl]benzophenones to 2-[3-[(phthalimido or methanesulfonyl)methyl]-4H-1,2,4-triazol-4-yl]benzophenones and converting these compounds to the highly active 6-phenyl-4H-s-triazolo[4,3-a][1,4]benzodiazepines useful as tranquilizers and sedatives.

3 Claims, No Drawings

2-[3-(PHTHALIMIDOMETHYL)-5-METHYL-4H-1,2,4-TRIAZOL-4-YL]BENZOPHENONES

This is a division of application Ser. No. 332,377, filed Feb. 14, 1973, now abandoned.

BACKGROUND OF THE INVENTION

FIELD OF THE INVENTION

This invention is directed to organic compounds and is particularly concerned with a novel process for the preparation of 6-phenyl-4H-s-triazolo[4,3-a][1,4]benzodiazepines and the intermediates thereof.

The novel process or production can be illustratively represented as follows:

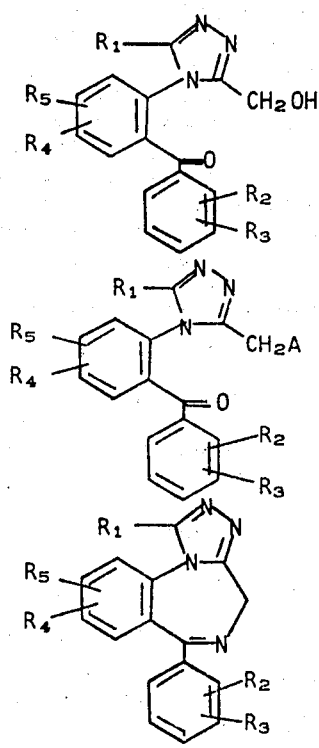

wherein A is selected from the group consisting of

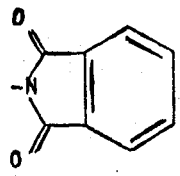

and

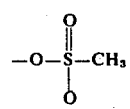

wherein $R_1$ is selected from the group consisting of hydrogen, alkyl of 1 to 3 carbon atoms, inclusive, phenyl, benzyl, and COOR' wherein R' is alkyl defined as above; and wherein $R_2$, $R_3$, $R_4$, and $R_5$ are selected from the group consisting of hydrogen, alkyl of 1 to 3 carbon atoms, inclusive, halogen, nitro, cyano, trifluoromethyl, and alkoxy, alkylthio, alkylsulfinyl, alkylsulfonyl, and alkanoylamino, in which the carbon chain moieties are of 1 to 3 carbon atoms, inclusive, and dialkylamino in which alkyl is defined as above.

The intermediates corresponding to formula II are specifically claimed.

The process of this invention comprises: treating a 2-[3-(hydroxymethyl)-4H-1,2,4-triazol-4-yl]benzophenone (I) with either methanesulfonyl chloride in the presence of a base (e.g. triethylamine, or other volatile tertiary amine) at −40° to +10° C. to obtain the compound II wherein

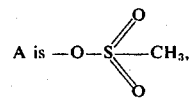

or treating I with phthalimide and triphenylphosphine in the presence of a hydrogen acceptor e.g. diethyl azodicarboxylate to give the compound II wherein A is

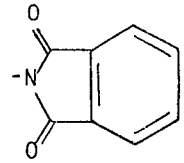

The compound of formula II

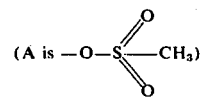

is then treated with gaseous ammonia, preferably in the presence of an alkali iodide, between 10° to 50° C. to give the compound III.

The compound of formula II wherein A is

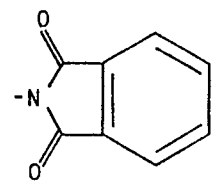

is treated with hydrazine hydrate in a lower alkanol (1 to 3 carbon atoms) for one to five hours at 25°–100° to give the corresponding compound of formula III above.

DESCRIPTION OF THE PREFERRED EMBODIMENT

Alkyl groups of 1 to 3 carbon atoms, inclusive, are exemplified by methyl, ethyl, propyl, and isopropyl.

The carbon chain moiety of alkoxy, alkylthio, alkylsulfinyl, alkylsulfonyl, dialkylamino which is of 1 to 3 carbon atoms, inclusive, is defined as lower-alkyl of 1 to 3 carbon atoms, inclusive, as above.

The alkanoylamino group of 1 to 3 carbon atoms consists of formamido

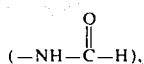

acetamido and propionamido.

The term halogen includes fluorine, chlorine, and bromine.

The compounds of the formula II are intermediates in the new synthesis of compounds of formula III, 6-phenyl-4H-s-triazolo[4,3-a][1,4]benzodiazepines. Compounds III are a new class of very potent sedatives and tranquilizers which have been recently invented and are described in detail by Hester et al. J. Medicinal Chemistry 14, 1078 (1971) and in Canadian Pat. No. 905,954.

The starting compounds of formula I of this invention are synthesized as shown in the Preparations.

In carrying out the process of this invention a selected compound I, preferably dissolved in an organic solvent is treated with methanesulfonyl chloride in the presence of a volatile, tertiary amine. Solvents useful in this reaction are chloroform, methylene chloride, ethylene dichloride, tetrahydrofuran, dioxane, mixtures thereof and the like. As tertiaryamine, triethylamine is preferred but any tertiary amine with a boiling point below about 150° C. and pK in the range of about 3 to about 5 can be used. The reaction is carried out at between −40° to 10° C., preferably between −20° and 0° C. The product II is recovered from the reaction mixture by conventional means e.g. extraction with an organic solvent such as chloroform, ether, methylene chloride or the like. Vacuum distillation is used to remove the solvent and to obtain the methanesulfonate II.

Compound II is dissolved in an organic solvent e.g. tetrahydrofuran, dioxane, ether or the like, and treated with ammonia (gas) or hexamethylenetetramine preferably after an alkali iodide, e.g. sodium or potassium iodide, has been added. After saturating the reaction mixture with ammonia, or after adding hexamethylenetetramine, the mixture is preferably stirred for from 4 to 48 hours at room temperature. The product III is obtained by conventional means, e.g. quenching the mixture, extraction, chromatography, crystallization, and the like.

When the intermediate II is a phthalimido derivative, the process consists of treating the starting material in a solvent with phthalimide in about equimolecular quantity or preferably with a slight excess of 5–20% of the calculated amounts and an equimolecular amount of triphenylphosphine, and a hydrogen acceptor; for example, a dialkyl azodicarboxylate, preferably diethyl azodicarboxylate. The reaction is carried out at temperatures between 0°–100° C. In the preferred embodiment of this reaction, temperatures between 20°–40° C. and stirring between 2–36 hours are used to complete the reaction. Solvents used are preferably water-free tetrahydrofuran, dioxane, 1,2-dimethoxyethane, ether, chloroform, methylene chloride and the like. At the termination of the reaction, the product II is recovered and purified in conventional manner, e.g. concentrating the reaction mixture, extraction, chromatography and recrystallization.

This product II is then treated with hydrazine hydrate in a lower alkanol e.g. methanol, ethanol, 1-propanol, or 2-propanol at a temperature of 25°–100° C. for 1 to 5 hours. Preferably, the temperature is kept between 65°–100° C. The product (III) is recovered and purified in conventional manner, e.g. extraction, chromatography crystallization and the like.

The following examples and preparations are illustrative of the processes and products of the present invention, but are not to be construed as limiting.

PREPARATION 1

2′-Benzoyl-4′-chloroacetanilide

Acetyl chloride (81.3 g., 1.037 mole) was added to a stirred solution of 2-amino-5-chlorobenzophenone (200.0 g., 0.864 mole) and pyridine (68.4 g., 0.864 mole) in dry ether (4 l.); the mixture was kept at ambient temperature for 2 hours and treated with 500 ml. of water. The layers were separated and the ether layer was dried over anhydrous sodium sulfate and concentrated. Crystallization of the residue from ethyl acetate-Skellysolve B hexanes gave: 124.0 g. of 2′-benzoyl-4′-chloroacetanilide of melting point 114°–115° C. Two more crops of 2′-benzoyl-4′-chloroacetanilide also were obtained: 67.8 g. of melting point 113.5°–114.5° C. and 33.0 g. of melting point 113°–114° C.

PREPARATION 2

6-Chloro-4-phenyl-2(1H)-quinoline

The procedure (reaction of 2′-benzoyl-5′-chloroacetanilide with sodium hydroxide) of A. E. Drukker and C. I. Judd, J., Heterocyclic Chem. 3, 359 (1966) was used for this preparation. The yield was 77 percent. Two other preparations have been described: S. C. Bell, T. S. Sulkowski, C. Gochman and S. J. Childress, J. Org. Chem. 27, 562 (1962); G. A. Reynolds and C. R. Hauser, J. Amer. Chem. Soc. 72, 1852 (1950).

PREPARATION 3

2,6-Dichloro-4-phenylquinoline

The procedure of A. E. Drukker and C. I. Judd, J. Heterocyclic Chem. 3, 359 (1966) was used for this preparation. The yield was 62%.

PREPARATION 4

6-Chloro-2-hydrazino-4-phenylquinoline

A stirred mixture of 2,6-dichloro-4-phenylquinoline (2.7 g., 0.01 mole) and hydrazine hydrate (6.8 g.) was refluxed under nitrogen for 1 hour and concentrated in vacuo. The residue was suspended in warm water, and the solid was collected by filtration, dried and recrystallized from ethyl acetate-Skelly B hexanes to give 1.81 g. (67%) yield) of 6-chloro-2-hydrazino-4-phenylquinoline of melting point 156.5°–157° C.

Anal. calcd. for $C_{15}H_{12}ClN_3$: C, 66.79; H, 4.49; Cl, 13.15; N, 15.58. Found: C, 67.15; H, 4.65; Cl, 13.19; N, 15.32.

PREPARATION 5

7-Chloro-1-methyl-5-phenyl-s-triazolo[4,3-a]-quinoline

A stirred mixture of 6-chloro-2-hydrazino-4-phenylquinoline (1.4 g., 0.0052 mole), triethyl orthoacetate (0.925 g., 0.0057 mole) and xylene (100 ml.) was refluxed, under nitrogen, for 2 hours 40 minutes. During this period the ethanol formed in the reaction was removed by distillation through a short, glass helix-packed column. The mixture was concentrated to dryness in vacuo and the residue was crystallized from methanol-ethyl acetate to give: 1.28 g. of 7-chloro-1-methyl-5-phenyl-s-triazolo[4,3-a]-quinoline of melting point 253.5°–255° C. (83.9% yield). The analytical sample was crystallized from methylene chloride: methanol and had a melting point 252.5°–253.5° C.

Anal. calcd. for $C_{17}H_{12}ClN_3$: C, 69.50; H, 4.12; Cl, 12.07; N, 14.31. Found: C, 69.38; H, 4.02; Cl, 12.10; N, 14.49.

PREPARATION 6

5-Chloro-2-(3-methyl-4H-1,2,4-triazol-4-yl)benzophenone (Oxidation of 7-chloro-1-methyl-5-phenyl-s-triazolo[4,3-a]quinoline)

A stirred suspension of 7-chloro-1-methyl-5-phenyl-s-triazolo[4,3-a]quinoline (2.94 g., 0.01 mole) in acetone (110 ml.) was cooled in an ice-bath and treated slowly with a solution prepared by adding sodium periodate (2 g.) to a stirred suspension of ruthenium dioxide (200 mg.) in water (35 ml.). The mixture became dark. Additional sodium periodate (8 g.) was added during the next 15 minutes. The ice bath was removed and the mixture was stirred for 45 minutes. Additional sodium periodate (4 g.) was added and the mixture was stirred at ambient temperature for 18 hours and filtered. The solid was washed with acetone and the combined filtrate was concentrated in vacuo. The residue was suspended in water and extracted with methylene chloride. The extract was dried over anhydrous potassium carbonate and concentrated. The residue was chromatographed on silica gel (100 g.) with 10% of methanol-90% ethyl acetate; 50 ml. fractions were collected. The product was eluted in fractions 10–20 and was crystallized from ethyl acetate to give: 0.405 g. of melting point 168°–169.5° C. and 0.291 g. of melting point 167.5°–169° (23.4% yield) of 5-chloro-2-(3-methyl-4H-1,2,4-triazol-4-yl)benzophenone, The analytical sample had a melting point of 168° C.

Anal. calcd. for $C_{16}H_{12}ClN_3O$: C, 64.54; H, 4.06; Cl, 11.91; N, 14.11. Found: C, 64.56; H, 4.35; Cl, 11.97; 11.93; N, 14.29.

PREPARATION 7

5-Chloro-2-[3-(hydroxymethyl)-5-methyl-4H-1,2,4-triazol-4-yl]benzophenone

A stirred mixture of 5-chloro-2-(3-methyl-4H-1,2,4-triazolo-4-yl)benzophenone, (2.98 g., 0.01 mole) paraformaldehyde (3 g.) and xylene (100 ml.) was warmed under nitrogen, in a bath maintained at 125° C. for 7 hours. The mixture was then concentrated in vacuo. The residue was chromatographed on silica gel (150 g.) with 3% methanol-97% chloroform. Fifty-ml. fractions were collected. The product was eluted in fractions 20–44. The fractions were concentrated and the residue was crystallized from ethanol-ethyl acetate to give: 1.64 g. of 5-chloro-2-[3-(hydroxymethyl)-5-methyl-4H-1,2,4-triazol-4-yl]benzophenone, of melting point 138°–142° C.; 0.316 g. of melting point 138.5°–141° C.; and 0.431 g. of melting point 139°–141° C., (72.8% yield). The analytical sample had a melting point of 138°–139° C.

Anal. calcd. for $C_{17}H_{14}ClN_3O_2$: C, 62.30; H, 4.30; Cl, 10.81; N, 12.82. Found: C, 62.23; H, 4.22; Cl, 10.82; N, 11.73.

PREPARATION 8

2'-(o-Chlorobenzoyl)-4'-chloroacetanilide

In the manner given in Preparation 1, 2-amino-2',5-dichlorobenzophenone, acetyl chloride and pyridine were reacted in ether to give 2'-(o-chlorobenzoyl)-4'-chloroacetanilide.

PREPARATION 9

6-chloro-4-(o-chlorophenyl)-2(1H)-quinolone

In the manner given in Preparation 2, 2'-(o-chlorobenzoyl)-4'-chloroacetanilide was reacted with sodium hydroxide to give 6-chloro-4-(o-chlorophenyl)-2(1H)-quinolone.

PREPARATION 10

2,6-dichloro-4-(o-chlorophenyl)quinoline

In the manner given by A. E. Drukker and C. I. Judd, J. Heterocyclic Chem. 3, 359 (1966), 6-chloro-4-(o-chlorophenyl)-2-(1H)-quinolone was chlorinated to give 2,6-dichloro-4-(o-chlorophenyl)quinoline.

PREPARATION 11

6-chloro-2-hydrazino-4-(o-chlorophenyl)-quinoline

In the manner given in Preparation 4, 2,6-dichloro-4-(o-chlorophenyl)quinoline was heated with hydrazine hydrate to give 6-chloro-2-hydrazino-4-(o-chlorophenyl)quinoline.

PREPARATION 12

7-Chloro-1-methyl-5-(o-chlorophenyl)-s-triazolo[4,3-a]quinoline

In the manner given in Preparation 5, 6-chloro-2-hydrazino-4-(o-chlorophenyl)quinoline and triethyl orthoacetate in xylene were refluxed to give 7-chloro-1-methyl-5-(o-chlorophenyl)-s-triazolo[4,3-a]quinoline.

PREPARATION 13

2',5-dichloro-2-(3-methyl-4H-1,2,4-triazol-4-yl)benzophenone.

In the manner given in Preparation 6, 7-chloro-1-methyl-5-(o-chlorophenyl)-s-triazolo[4,3-a]quinoline in acetone was oxidized with sodium periodate and ruthenium dioxide to give 2',5-dichloro-2-(3-methyl-4H-1,2,4-triazolo-4-yl)benzophenone of melting point 147.5°–148.5° C.

Anal. calcd. for $C_{16}H_{11}Cl_2N_3O$: C, 57.85; H, 3.34; Cl, 21.35; N, 12.65. Found: C, 57.70; H, 3.21; Cl, 21.58; N, 12.47.

PREPARATION 14

2',5-dichloro-2-[3-(hydroxymethyl)-5-methyl-4H-1,2,4-triazol-4-yl]benzophenone

In the manner given in Preparation 7, 2',5-dichloro-2-(3-methyl-4H-1,2,4-triazol-4-yl)benzophenone was treated at 125° C. in xylene with paraformaldehyde to give 2',5-dichloro-2-[3-(hydroxymethyl)-5-methyl-4H-1,2,4-triazol-4-yl]benzophenone of melting point 193.5°–195° C.

In the same manner given in the prior Preparations other starting compounds of formula 1 can be made. Representative compounds thus obtained include:

2'-chloro-5-nitro-2-[3-(hydroxymethyl)-5-methyl-4H-1,2,4-triazol-4-yl]benzophenone;
5-chloro-2-[3-(hydroxymethyl)-5-ethyl-4H-1,2,4-triazol-4-yl]benzophenone;
5-chloro-2-[3-(hydroxymethyl)-5-phenyl-4H-1,2,4-triazol-4-yl]benzophenone;
5-chloro-2-[3-(hydroxymethyl)-5-benzyl-4H-1,2,4-triazol-4-yl]benzophenone;
2',6'-difluoro-5-(methylthio)-2-[3-(hydroxymethyl)-5-propyl-4H-1,2,4-triazol-4-yl]benzophenone;
5-bromo-2'-chloro-2-[3-(hydroxymethyl)-4H-1,2,4-triazol-4-yl]benzophenone;
2'-chloro-5-fluoro-2-[3-(hydroxymethyl)-4H-1,2,4-triazol-4-yl]benzophenone;
2'-chloro-6-cyano-2-[3-(hydroxymethyl)-5-carbomethoxy-4H-1,2,4-triazol-4-yl]benzophenone;
2'-chloro-4-diethylamino-2-[3-(hydroxymethyl)-5-methyl-4H-1,2,4-triazol-4-yl]benzophenone;
2'-chloro-5-(methylthio)-2-[3-(hydroxymethyl)-5-methyl-4H-1,2,4-triazol-4-yl]benzophenone;
2'-chloro-3-formamido-2-[3-(hydroxymethyl)-5-ethyl-4H-1,2,4-triazol-4-yl]benzophenone;
2'-chloro-4-(ethylsulfinyl)-2-[3-(hydroxymethyl)-5-phenyl-4H-1,2,4-triazol-4-yl]benzophenone;
2'-chloro-5-(propylsulfonyl)-2-[3-(hydroxymethyl)-5-carbopropoxy-4H-1,2,4-triazol-4-yl]benzophenone;
6-methyl-3'-(propylthio)-2-[3-(hydromethyl)-4H-1,2,4-triazol-4-yl]benzophenone;
2'-(dimethylamino)-4-isopropyl-2-[3-(hydroxymethyl)-4H-1,2,4-triazol-4-yl]benzophenone;
2'-chloro-4,5-dicyano-2-[3-(hydroxymethyl)-5-methyl-4H-1,2,4-triazol-4-yl]benzophenone;
3'-(ethylsulfinyl)-3,5-dipropyl-2-[3-(hydroxymethyl)-5-methyl-4H-1,2,4-triazol-4-yl]benzophenone;
5-chloro-2'-acetamido-2-[3-(hydroxymethyl)-5-methyl-4H-1,2,4-triazol-4-yl]benzophenone;
5-chloro-2-[3-(hydroxymethyl)-4H-1,2,4-triazol-4-yl]benzophenone;
2'-chloro-2-[3-(hydroxymethyl)-4H-1,2,4-triazol-4-yl]benzophenone;
2',5-dichloro-2-[3-(hydroxymethyl)-4H-1,2,4-triazol-4-yl]-benzophenone;
2-[3-(hydroxymethyl)-4H-1,2,4-triazol-4-yl]benzophenone;
2-[3-(hydroxymethyl)-5-methyl-4H-1,2,4-triazol-4-yl]benzophenone;

and the like.

EXAMPLE 1

8-Chloro-1-methyl-6-phenyl-4H-s-triazolo[4,3-a]-[1,4]benzodiazepine

A solution of 0.328 g. (1.00 mmol.) of 5-chloro-2-[3-(hydroxymethyl)-5-methyl-4H-1,2,4-triazol-4-yl]benzophenone dissolved in 5.0 ml. of hydrocarbon-stabilized-chloroform was cooled to −20° C. in a Dry Ice acetone bath, treated with 0.206 ml. (0.150 g., 1.5 mmol.) of triethylamine, and stirred for 5 minutes. The solution was treated dropwise with 0.106 ml. (1.3 mmol.) of methanesulfonyl chloride and stirred for 10 minutes. Ammonia gas was introduced to the atmosphere above the cold solution. Immediately a white precipitate appeared. Stirring was maintained at −20° C. for 10 minutes after which the temperature was gradually raised to 25° C. After 20 minutes, 3 ml of freshly distilled tetrahydrofuran and 0.332 g. (2.00 mmol.) of potassium iodide was added and the resulting mixture was stirred overnight (24 hrs.). The reaction mixture was quenched in a 5% aqueous sodium hydroxide solution, extracted with chloroform, dried over anhydrous sodium sulfate and concentrated in vacuo to yield an oil. On trituration with ethyl acetate, fine, white needles of 8-chloro-1-methyl-6-phenyl-4H-s-triazolo[4,3-a][1,4]benzodiazepine were deposited. This was recrystallized from ethyl acetate to yield 30 mg. of white needles of melting point 228°–230° C. and 15 mg., of melting point 215°–223°.

Instead of ammonia hexamethylenetetramine can be used.

EXAMPLE 2

8-Chloro-1-methyl-6-(o-chlorophenyl)-4H-s-triazolo[4,3-a][1,4]benzodiazepine

A suspension of 0.363 g. (1.00 mmol.) of 2',5-dichloro-2-[3-(hydroxymethyl)-5-methyl-4H-1,2,4-triazol-4-yl]benzophenone in 5.0 ml. of methylene chloride was cooled to −20° C. in a Dry Ice/acetone bath and treated with 0.206 ml. (0.150 g., 1.50 mmol.) of triethylamine, followed by dropwise addition of 0.106 ml. (1.3 mmol.) of methanesulfonyl chloride. (Most of the starting material dissolved during the addition of the methanesulfonyl chloride.) During 15 minutes the temperature was gradually raised to 0°. The reaction mixture was quenched on ice and extracted with methylene chloride. The organic extracts were treated with a saturated aqueous sodium bicarbonate solution, dried over anhydrous sodium sulfate and concentrated in vacuo to yield an oil. The oil was dissolved in 5 ml. of freshly distilled tetrahydrofuran in a dry flask and treated first with 0.332 g. (2.00 mmol.) of potassium iodide, then ammonia (gas). After saturating the reaction mixture with ammonia, the mixture was warmed to room temperature (22°–24° C.) and stirred for 24 hours. The mixture was quenched in a saturated aqueous sodium hydroxide solution, extracted with chloroform, dried over anhydrous sodium sulfate and concentrated in vacuo to afford an oil. Crystallization from ethyl acetate and methanol/ethyl acetate yielded 25 mg. of a tan solid of melting point 210°–221° C. Recrystallization from ethyl acetate gave pure 8-chloro-1-methyl-6-(o-chlorophenyl)-4H-s-triazolo[4,3-a][1,4]benzodiazepine of melting point 223°–225° C.

EXAMPLE 3

5-Chloro-2-[3-(phthalimidomethyl)-5-methyl-4H-1,2,4-triazol-4-yl]benzophenone.

A stirred mixture of 5-chloro-2-[3-(hydroxymethyl)-5-methyl-4H-1,2,4-triazol-4-yl]benzophenone (0.656 g., 0.002 mole), phthalimide (0.324 g., 0.0022 mole), triphenylphosphine (0.576 g., 0.0022 mole) and dry tetrahydrofuran (20 ml.), under nitrogen, was treated with diethyl azodicarboxylate (0.383 g., 0.0022 mole) and stirred at ambient temperature for 23 hours. It was concentrated in vacuo and the residue was chromatographed on silica gel (75 g.) with 1.5% methanol 98.5% chloroform; 10 ml. fractions were collected. The product was eluted in fractions 31-57 and crystallized from methanol-ethyl acetate to give 0.148 g. of 5-chloro-2-[3-(phthalimidomethyl)-5-methyl-4H-1,2,4-triazol-4- yl]benzophenone of melting point 217.5°–219° C.; 0.257 g. of product of melting point 219°–220°; 0.189 g. of melting point 218.5°–220° C. and 0.082 g. of melting point 219°–220.5° of 5-chloro-2-[3-(phthalimidomethyl)-5-methyl-4H-1,2,4-triazol-4-yl]benzophenone.

The analytical sample had a melting point of 219°–221°.

Anal. calcd. for $C_{25}H_{17}ClN_4O_3$: C, 65.72; H, 3.75; Cl, 7.76; N, 12.26. Found: C, 65.86; H, 3.83; Cl, 7.72; N, 12.63.

Alternatively 2-[3-(phthalimidomethyl)-4H-1,2,4-triazol-4-yl]benzophenones of formula II, A=

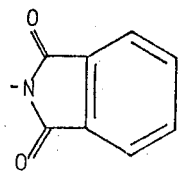

can be prepared from 3-amino-3,4-dihydro-4-hydroxy-4-phenylquinazolines of formula IV by allowing a compound of formula IV to react with an activated derivative of phthaloylglycine, e.g. the acid chloride, mixed anhydride or imidazolide, and then warming the resulting product in acetic acid to give a compound of formula II, A is

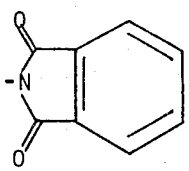

The 3-amino-3,4-dihydro-4-hydroxy-4-phenylquinazolines (IV) may be prepared as described in the literature for 3-amino-6-chloro-3,4-dihydro-4-hydroxy-4-phenylquinazoline by M. E. Derieg et al., J. Org. Chem. 36, 782 (1971):

wherein $R_1$, $R_2$, $R_3$, $R_4$, and $R_5$ have the same significance as in formula II; wherein $$X \text{ is Cl, Br, } -O-\overset{\overset{O}{\|}}{C}-OC_2H_5,$$

or

and wherein A is

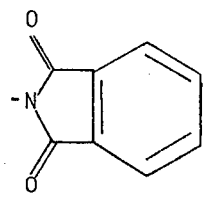

EXAMPLE 4

5-Chloro-2-[3-(phthalimidomethyl)-5-methyl-4H-1,2,4-triazol-4-yl]benzophenone

A stirred solution of phthaloylglycine (2.26 g., 0.01 mole) in dry tetrahydrofuran (20 ml.), under nitrogen, was cooled in an ice-bath and treated with carbonyl-

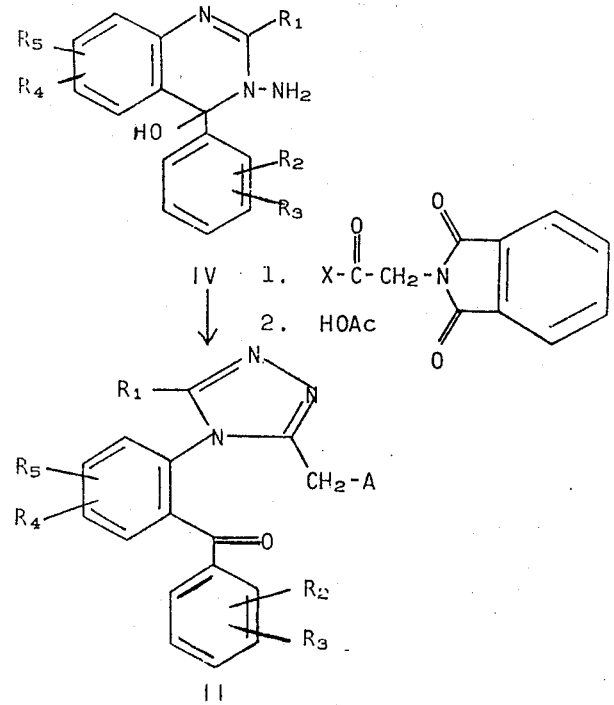

diimidazole. This mixture was kept at ambient temperature (22°–24°) for 1.5 hours, cooled in an ice bath and treated with a mixture of 3-amino-6-chloro-3,4-dihydro-4-hydroxy-4-phenylquinazoline (2.88 g., 0.01 mole) in tetrahydrofuran (25 ml.). This mixture was kept at ambient temperature for 42 hours and concentrated in vacuo. The residue was mixed with a dilute sodium bicarbonate solution and extracted with methylene chloride. The extract was washed with a saturated sodium chloride solution, dried over anhydrous sodium sulfate and concentrated to give a crude oil. This oil was mixed with acetic acid (50 ml.) and warmed in an oil bath at 120° for 1 hour. The acetic acid was then concentrated in vacuo and the residue was mixed with water, neutralized with sodium bicarbonate and extracted with methylene chloride. The extract was washed with water, dried over anhydrous sodium sulfate and concentrated. The residue was chromatographed over silica gel (400 g.) with 2.5% methanol-97.5% chloroform. The product obtained from the column was crystallized from methylene chloride-ethyl acetate to give 0.24 g. of 5-chloro-2-[3-(phthalimidomethyl)-5-methyl-4H-1,2,4-triazol-4-yl]benzophenone of melting point 215°–218° C. An additional 0.135 g. of this product of melting point 216°–218.5° C. was obtained by working up the mother liquors.

EXAMPLE 5

8-Chloro-1-methyl-6-phenyl-4H-s-triazolo[4,3-a]-[1,4]benzodiazepine

A stirred mixture of 5-chloro-2-[3-(phthalimidomethyl)-5-methyl-4H-1,2,4-triazol-4-yl]benzophenone (0.257 g., 0.562 mmole) and absolute ethanol (3 ml.) was treated with hydrazine hydrate (0.05 ml., 1.04 mmole) and warmed in an oil bath at 73° C. for 80 minutes. (The solution precipitated a white solid after 30 minutes.) The cooled mixture was mixed with water and extracted with chloroform. The extract was washed with brine, dried over anhydrous sodium sulfate and concentrated. The residue was chromatographed on silica gel (42 g.) with 2% methanol-98% chloroform; 10 ml. fractions were collected. The product was eluted in fractions 33-57 and crystallized from ethyl acetate to give 77 mg., of melting point 229°–230° C. and 26 mg., of melting point 228°–229.5° C. of 8-chloro-1-methyl-6-phenyl-4H-s-triazolo[4,3-a][1,4]benzodiazepine.

Anal. calcd. for $C_{17}H_{13}ClN_4$: C, 66.13; H, 4.24; Cl, 11.48; N, 18.15. Found: C, 66.05; H, 4.13; Cl, 11.34; N, 18.00.

EXAMPLE 6

8-Chloro-1-methyl-6-(2,6-difluorophenyl)-4H-s-triazolo[4,3-a][1,4]benzodiazepine In the manner given in Example 1, 2',6'-difluoro-5-chloro-2-[3-(hydroxymethyl)-5-methyl-4H-1,2,4-triazol-4-yl]-benzophenone was treated with methanesulfonyl chloride and triethylamine in chloroform. The resulting solution was then treated with ammonia (gas) to give 8-chloro-1-methyl-6-(2,6-difluorophenyl)-4H-s-triazolo[4,3-a][1,4]benzophenone.

EXAMPLE 7

8-Chloro-6-phenyl-4H-s-triazolo[4,3-a][1,4]-benzodiazepine

In the manner given in Example 1, 5-chloro-2-[3-(hydroxymethyl)-4H-1,2,4-triazol-4-yl]benzophenone was treated with methanesulfonyl chloride and triethylamine in chloroform. The resulting solution was then treated with ammonia (gas) to give 8-chloro-6-phenyl-4H-s-triazolo[4,3-a][1,4]-benzophenone.

EXAMPLE 8

6-(o-chlorophenyl)-4H-s-triazolo[4,3-a][1,4]benzodiazepine

In the manner given in Example 1, 2'-chloro-2-[3-(hydroxymethyl)-4H-1,2,4-triazol-4-yl]benzophenone was treated with methanesulfonyl chloride and triethylamine in chloroform. The resulting solution was then treated with ammonia (gas) to give 6-(o-chlorophenyl)-4H-s-triazolo[4,3-a][1,4]-benzophenone.

EXAMPLE 9

8,10-Dicyano-1-methyl-6-(m-nitrophenyl)-4H-s-triazolo[4,3-a][1,4]benzodiazepine

In the manner given in Example 1, 3,5-dicyano-3'-nitro-2-[3-(hydroxymethyl)-5-methyl-4H-1,2,4-triazol-4-yl]-benzophenone was treated with methanesulfonyl chloride and triethylamine in chloroform. The resulting solution was then treated with ammonia (gas) to give 8,10-dicyano-1-methyl-6-(m-nitrophenyl)-4H-s-triazolo[4,3-a][1,4]benzophenone.

EXAMPLE 10

1-ethyl-8-bromo-6-(2,4-diethylphenyl)-4H-s-triazolo[4,3-a][1,4]benzodiazepine

In the manner given in Example 1, 5-bromo-2',4'-diethyl-2-[3-(hydroxymethyl)-5-ethyl-4H-1,2,4-triazol-4-yl]benzophenone was treated with methanesulfonyl chloride and triethylamine in chloroform. The resulting solution was then treated with ammonia (gas) to give 1-ethyl-8-bromo-6-(2,4-diethylphenyl)-4H-s-triazolo[4,3-a][1,4]-benzophenone.

EXAMPLE 11

1-Benzyl-8-trifluoromethyl-6-(o-chlorophenyl)-4H-s-triazolo[4,3-a][1,4]benzodiazepine In the manner given in Example 1, 5-trifluoromethyl-2'-chloro-2-[3-(hydroxymethyl)-5-benzyl-4H-1,2,4-triazol-4-yl]benzophenone was treated with methanesulfonyl chloride and triethylamine in chloroform. The resulting solution was then treated with ammonia (gas) to give 1-benzyl-8-trifluoromethyl-6-(o-chlorophenyl)-4H-s-triazolo[4,3-a][1,4]-benzophenone.

EXAMPLE 12

1-Propyl-9-(ethylsulfonyl)-6-[p-(diethylamino)-phenyl]-4H-s-triazolo[4,3-a][1,4]benzodiazepine In the manner given in Example 1, 4-(ethylsulfonyl)-4'-(diethylamino)-2-[3-(hydroxymethyl)-5-propyl-4H-1,2,4-triazol-4-yl]benzophenone was treated with methanesulfonyl chloride and triethylamine in chloroform. The resulting solution was then treated with ammonia (gas) to give 1-propyl-9-(ethylsulfonyl)-6-[p-

(diethylamino)phenyl]-4H-s-triazolo[4,3-a][1,4]benzophenone.

EXAMPLE 13

1-Phenyl-7-propyl-6-(o-bromophenyl)-4H-s-triazolo[4,3-a][1,4]benzodiazepine

In the manner given in Example 1, 6-propyl-2'-bromo-2-[3-(hydroxymethyl)-5-phenyl-4H-1,2,4-triazol-4-yl]benzophenone was treated with methanesulfonyl chloride and triethylamine in chloroform. The resulting solution was then treated with ammonia (gas) to give 1-phenyl-7-propyl-6-(o-bromophenyl)-4H-s-triazolo[4,3-a][1,4]benzophenone.

EXAMPLE 14

8-nitro-1-methyl-6-(o-chlorophenyl)-4H-s-triazolo[4,3-a][1,4]benzodiazepine

In the manner given in Example 3, a mixture of 5-nitro-2'-chloro-2-[3-(hydroxymethyl)-5-methyl-4H-1,2,4-triazol-4-yl]benzophenone, phthalimide and triphenylphosphine in tetrahydrofuran was treated with diethyl azodicarboxylate to give 5-nitro-2'-chloro-2-[3-(phthalimidomethyl)-5-methyl-4H-1,2,4-triazol-4-yl]benzophenone.

In the manner given in Example 4, 5-nitro-2'-chloro-2-[3-(phthalimidomethyl)-5-methyl-4H-1,2,4-triazol-4-yl]benzophenone was heated in ethanol with hydrazine hydrate to give 8-nitro-1-methyl-6-(o-chlorophenyl)-4H-s-triazolo-[4,3-a][1,4]benzodiazepine.

EXAMPLE 15

8-Fluoro-1-ethyl-6-[p-(propylsulfinyl)phenyl]-4H-s-triazolo[4,3-a][1,4]benzodiazepine In the manner given in Example 3, a mixture of 5-fluoro-4'-(propylsulfinyl)-2-[3-(hydroxymethyl-5-ethyl-4H-1,2,4-triazol-4-yl]benzophenone, phthalimide and triphenylphosphine in dioxane was treated with diethyl azodicarboxylate to give 5-fluoro-4'-(propylsulfinyl)-2-[3-(phthalimidomethyl)-5-ethyl-4H-1,2,4-triazol-4-yl]benzophenone.

In the manner given in Example 5, 5-fluoro-4'-(propylsulfinyl)-2-[3-(phthalimidomethyl)-5-ethyl-4H-1,2,4-triazol-4-yl]benzophenone was heated in ethanol with hydrazine hydrate to give 8-fluoro-1-ethyl-6-[p-(propylsulfinyl)phenyl]-4H-s-triazolo[4,3-a][1,4]benzodiazepine.

EXAMPLE 16

8-Methylthio-1-methyl-6-(o-chlorophenyl)-4H-s-triazolo[4,3-a][1,4]benzodiazepine In the manner given in Example 3, a mixture of 5-methylthio-2,-chloro-2-[3-(hydroxymethyl)-5-methyl-4H-1,2,4-triazol-4-yl]benzophenone, phthalimide and triphenylphosphine in tetrahydrofuan was treated with diethyl azodicarboxylate to give 5-methylthio-2'-chloro-2-[3-(phthalimidomethyl)-5-methyl-4H-1,2,4-triazol-4-yl]benzophenone.

In the manner given in Example 5, 5-methylthio-2'-chloro-2-[3-(phthalimidomethyl)-5-methyl-4H-1,2,4-triazol-4-yl]benzophenone was heated in ethanol with hydrazine hydrate to give 8-methylthio-1-methyl-6-(o-chlorophenyl)-4H-s-triazolo[4,3-a][1,4]benzodiazepine.

EXAMPLE 17

1-Phenyl-9-ethoxy-8-isopropyl-6-[m-(methylthio)phenyl]-4H-s-triazolo[4,3-a][1,4]benzodiazepine In the manner given in Example 3, a mixture of 4-ethoxy-5-isopropyl-3'-methylthio-2-[3-(hydroxymethyl)-5-phenyl-4H-1,2,4-triazol-4-yl]benzophenone, phthalimide and triphenylphosphine in tetrahydrofuran was treated with diethyl azodicarboxylate to give 4-ethoxy-5-isopropyl-3'-methylthio-2-[3-(phthalimidomethyl)-5-phenyl-4H-1,2,4-triazol-4-yl]benzophenone.

In the manner given in Example 5, 4-ethoxy-5-isopropyl-3'-methylthio-2-[3-(phthalimidomethyl)-5-phenyl-4H-1,2,4-triazol-4-yl]benzophenone was heated in ethanol with hydrazine hydrate to give 1-phenyl-9-ethoxy-8-isopropyl-6-[m-(methylthio)phenyl]-4H-s-triazolo[4,3-a][1,4]benzodiazepine.

EXAMPLE 18

1-propyl-8-isopropylsulfonyl-6-(o-fluorophenyl)-4H-s-triazolo[4,3-a][1,4]benzodiazepine In the manner given in Example 3, a mixture of 5-isopropylsulfonyl-2'-fluoro-2-[3-(hydroxymethyl)-5-propyl-4H-1,2,4-triazol-4-yl]benzophenone, phthalimide and triphenylphosphine in tetrahydrofuran was treated with diethyl azodicarboxylate to give 5-isopropylsulfonyl-2'-fluoro-2-[3-(phthalimidomethyl)-5-propyl-4H-1,2,4-triazol-4-yl]benzophenone.

In the manner given in Example 5, a solution of 5-isopropylsulfonyl-2'-fluoro-2-[3-(phthalimidomethyl)-5-propyl-4H-1,2,4-triazol-4-yl]benzophenone in methanol was heated with hydrazine hydrate to give 1-propyl-8-isopropylsulfonyl-6-(o-fluorophenyl)-4H-s-triazolo[4,3-a][1,4]-benzodiazepine.

EXAMPLE 19

1-Benzyl-7-formamido-6-(o-chlorophenyl)-4H-s-triazolo[4,3-a][1,4]benzodiazepine

In the manner given in Example 3, a mixture of 6-formamido-2'-chloro-2-[3-(hydroxymethyl)-5-benzyl-4H-1,2,4-triazol-4-yl]benzophenone, phthalimide and triphenylphosphine in tetrahydrofuran was treated with diethyl azodicarboxylate to give 6-formamido-2'-chloro-2-[3-(phthalimidomethyl)-5-benzyl-4H-1,2,4-triazol-4-yl]benzophenone.

In the manner given in Example 5, 6-formamido-2'-chloro-2-[3-(phthalimidomethyl)-5-benzyl-4H-1,2,4-triazol-4-yl]benzophenone was heated in ethanol with hydrazine hydrate to give 1-benzyl-7-formamido-6-(o-chlorophenyl)-4H-s-triazolo[4,3-a][1,4]benzodiazepine.

EXAMPLE 20

8-chloro-1-methyl-6-(o-chlorophenyl)-4H-s-triazolo[4,3-a][1,4]benzodiazepine

In the manner given in Example 3, a mixture of 2',5-dichloro-2-[3-(hydroxymethyl)-5-methyl-4H-1,2,4-triazol-4-yl]benzophenone, phthalimide and triphenylphosphine in tetrahydrofuran was treated with diethyl azodicarboxylate to give 2',5-dichloro-2-[3-(phthalimidomethyl)-5-methyl-4H-1,2,4-triazol-4-yl]benzophenone of melting point 262°–265°C.

Anal. calcd. for $C_{25}H_{16}Cl_2N_4O_3$: C, 61.11; H, 3.28; Cl, 14.43; N, 11.40. Found: C, 60.77; H, 3.26; Cl, 14.49; N, 11.45.

In the manner given in Example 4, 2',5-dichloro-2-[3-(phthalimdomethyl)-5-methyl-4H-1,2,4-triazol-4-yl]benzophenone was heated in ethanol with hydrazine hydrate to give 8-chloro-1-methyl-6-(o-chlorophenyl)-4H-s-triazolo[4,3-a]-[1,4]benzodiazepine of melting point 223°–225°C.

Varying the method in which A of compound III is a methanesulfonyl group

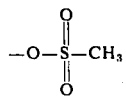

by using for the step II → III a substituted amine produces open-chain benzophenones of the formula V

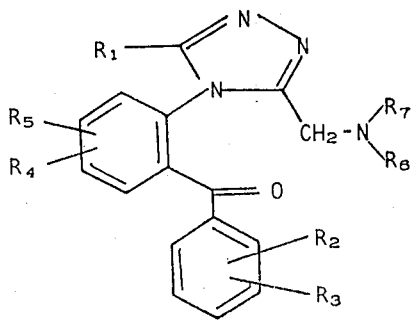

wherein $R_1$, $R_2$, $R_3$, $R_4$, and $R_5$ have the same significance as in formula II and wherein $R_6$ and $R_7$ are alkyl of 1 to 3 carbon atoms, inclusive, or together

is a heterocyclic amine, e.g. pyrrolidino, 4-methylpiperazino, piperidino, or morpholino. The resulting compounds also have tranquilizing and sedative activity in dosages of 0.1 to 5 mg./kg.

EXAMPLE 21

5-Chloro-2-[3-methyl-5-(pyrrolidinomethyl)-4H-1,2,4-triazol-4-yl]benzophenone

A solution of 0.328 g. (1.00 mmol.) of 5-chloro-2-[3-methyl-5-(hydroxymethyl)-4H-1,2,4-triazol-4-yl]benzophenone dissolved in 5.0 ml. of methylene chloride was cooled to 0°C. in an ice bath. Triethylamine (0.150 g., 1.5 mmol.) was added and the solution was stirred for 5 minutes at 0°C. Cautiously, and dropwise over 4 minutes, 0.106 ml. (1.3 mmol.) of methanesulfonyl chloride was added and the solution was stirred for 20 minutes. The reaction was quenched on ice and extracted with a saturated aqueous sodium bicarbonate solution, dried over anhydrous sodium sulfate and concentrated in vacuo. The resulting oil, dissolved in 4.0 ml. of freshly distilled tetrahydrofuran, was treated at 0°C. with 0.332 g. (2.0 mmol.) of potassium iodide followed by 1.0 ml. of pyrrolidine. The mixture was stirred at 0°C. for 10 minutes then warmed to room temperature and stirred overnight. The mixture was quenched in an aqueous 5% sodium hydroxide solution and the product was extracted with chloroform. The chloroform layer was dried over anhydrous sodium sulfate and concentrated in vacuo to yield a yellow oil which crystallized from ethyl acetate to afford 200 mg. of 5-chloro-2-[3-methyl-5-(pyrrolidinomethyl)-4H-1,2,4-triazol-4-yl]benzophenone in the form of fine white needles of melting point 174°–176°C.

Anal. calcd. for $C_{21}H_{21}ClN_4O$: C, 66.22; H, 5.56; N, 14.71; Cl, 9.31. Found: C, 65.96; H, 5.62; N, 14.68; Cl, 9.31.

EXAMPLE 22

5-Chloro-2-[3-methyl-5-[N-(4-methylpiperazino)methyl]-4H-1,2,4-triazol-4-yl]benzophenone, oxalate salt A solution of 1.312 g. (4.00 mmol.) of 5-chloro-2-[3-methyl-5-(hydroxymethyl)-4H-1,2,4-triazol-4-yl]benzophenone, dissolved in 20 ml. of methylene chloride, was cooled to 0°C. and treated with 0.825 ml. (6.00 mmol.) of triethylamine. Methanesulfonyl chloride (0.424 ml., 5.5 mmol.) was added dropwise over a period of 5 minutes via a syringe and the resulting solution was stirred for 20 minutes. The solution was dissolved in additional methylene chloride and extracted with ice-water followed by an aqueous sodium bicarbonate solution. The organic layer was dried over anhydrous sodium sulfate and concentrated in vacuo to yield an oil. The oil was dissolved in 20 ml. of tetrahydrofuran, cooled to 0°C. and treated with 1.33 g. (8.0 mmol.) of potassium iodide followed by 4.0 ml. of 1-methylpiperazine. The mixture was quenched in a cold 5% aqueous sodium hydroxide solution and extracted twice with chloroform. The chloroform extracts were combined, washed with water, dried over anhydrous sodium sulfate and concentrated in vacuo to yield a yellow oil. The oil was crystallized with difficulty as an oxalate salt by treating with 1 g. of oxalic acid in 10 ml. of ethanol, followed by cooling to 0°C. An amorphous solid (1.7 g., m.p. 190°–192°C. decomp.) was obtained. An analytical sample had a melting point 190°–191°C. (decomp.).

Anal. Calcd. For $C_{22}H_{24}ClN_5O_3(COOH)_2$: C, 49.45; H, 4.45; N, 10.30; Cl, 5.21. Found: C, 49.32; H, 4.52; N, 10.82; Cl, 5.33.

EXAMPLE 23

5-Chloro-2-[3-methyl-5-[(dimethylamino)methyl]-4H-1,2,4-triazol-4-yl]benzophenone.

In the manner given in Example 21, 5-chloro-[3-methyl-5-(hydroxymethyl)-4H-1,2,4-triazol-4-yl]benzophenone was reacted with methanesulfonyl chloride in the presence of triethylamine and the resulting solution, treated with gaseous dimethylamine in the presence of potassium iodide, to give 5-chloro-2-[3-methyl-5-(dimethylamino)methyl]-4H-1,2,4-triazol-4-yl]benzophenone of melting point 171°–172°.

EXAMPLE 24

8-Chloro-1-methyl-6-phenyl-4H-s-triazolo-[4,3-a][1,4]benzodiazepine

5-Chloro-2-[3-[(methylsulfonyloxy)methyl]-5-methyl-4H-1,2,4-triazol-4-yl]benzophenone (5 g.) (see Example 1), dissolved in water-free tetrahydrofuran, was treated with 4 g. of hexamethylenetetramine 1 g. of potassium iodide and 20 ml. of ethanol. The mixture was refluxed for 15 hours, then cooled, filtered, and the filtrate evaporated to dryness to give a yellow gum. The gum was dissolved in chloroform, the chloroform solution extracted with water then chromatographed over 300 g. of Silica Gel and 3% methanol-97% chloroform. Fractions 52–132 gave a colorless oil which upon recrystallization from ethylacetate gave 800 mg. of 8-chloro-1-methyl-6-phenyl-4H-s-triazolo-[4,3-a][1,4]benzodiazepine.

I claim:
1. A compound of the formula:

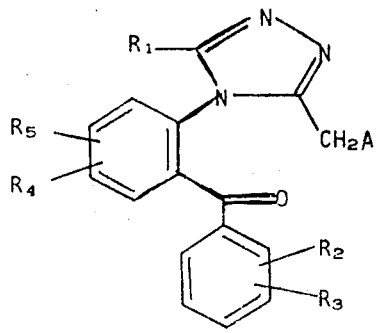

wherein A is

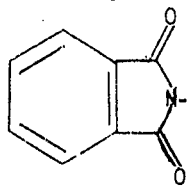

wherein $R_1$ is selected from the group consisting of hydrogen, alkyl of 1 to 3 carbon atoms, inclusive, phenyl, benzyl, and wherein $R_2$, $R_3$, $R_4$, and $R_5$ are selected from the group consisting of hydrogen, alkyl as defined above, halogen, nitro, cyano, trifluoromethyl, and alkoxy, alkylthio, alkylsulfinyl, alkylsulfonyl, and alkanoylamino in which the carbon moiety is between 1 to 3 carbon atoms, inclusive, and dialkylamino in which alkyl is defined as above.

2. A compound according to claim 1 wherein $R_1$ is methyl, $R_4$ is 5-chloro, $R_2$, $R_3$, and $R_5$ are hydrogen, and the compound is therefore 5-chloro-2-[3-(phthalimidomethyl)-5-methyl-4H-1,2,4-triazol-4-yl]benzophenone.

3. A compound according to claim 1 wherein $R_1$ is methyl, $R_2$ is o-chloro, $R_4$ is 5-chloro, $R_3$ and $R_5$ are hydrogen and the compound is therefore 2′,5-dichloro-2-[3-(phthalimidomethyl)-5-methyl-4H-1,2,4-triazol-4-yl]benzophenone.

* * * * *